(12) United States Patent
Gerke et al.

(10) Patent No.: US 9,068,151 B2
(45) Date of Patent: Jun. 30, 2015

(54) PHOTOLABILE PRO-FRAGRANCES

(71) Applicant: Henkel AG & Co. KGaA, Duesseldorf (DE)

(72) Inventors: Thomas Gerke, Duesseldorf (DE); Christian Kropf, Hilden (DE); Ursula Huchel, Cologne (DE); Axel Griesbeck, Cologne (DE); Olga Mayer, Mannheim (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 14/140,604

(22) Filed: Dec. 26, 2013

(65) Prior Publication Data

US 2014/0113849 A1    Apr. 24, 2014

Related U.S. Application Data

(63) Continuation of application No. PCT/EP2012/060471, filed on Jun. 4, 2012.

(30) Foreign Application Priority Data

Jun. 30, 2011 (DE) .................. 10 2011 078 416

(51) Int. Cl.
    *C11D 3/50*    (2006.01)
    *C07C 403/24*  (2006.01)
    *C07C 45/69*   (2006.01)
    *C07C 49/798*  (2006.01)
    *C07C 49/15*   (2006.01)

(52) U.S. Cl.
    CPC ............ *C11D 3/507* (2013.01); *C07C 2101/16* (2013.01); *C07C 45/69* (2013.01); *C07C 49/798* (2013.01); *C07C 49/15* (2013.01)

(58) Field of Classification Search
    CPC ...... C11D 3/0063; C11D 3/2072; C11D 3/50; C11D 7/264; C07C 403/24
    USPC ............. 510/102, 105; 568/303, 308; 512/21
    See application file for complete search history.

(56) References Cited

U.S. PATENT DOCUMENTS

| | | | |
|---|---|---|---|
| 6,949,680 B2 | 9/2005 | Herrmann | |
| 8,129,569 B2 | 3/2012 | Huchel et al. | |
| 8,466,294 B2 | 6/2013 | Huchel et al. | |
| 2003/0078239 A1* | 4/2003 | Dasseux et al. | ............... 514/102 |
| 2003/0129212 A1 | 7/2003 | Herrmann | |
| 2011/0237685 A1 | 9/2011 | Huchel et al. | |

OTHER PUBLICATIONS

PCT International Search Report (PCT/EP2012/060471) dated Aug. 29, 2012.
Parkes et al., "The Preparation of p-Di-(6-carboxyhexanoyl)benzene", Journal of the Chemical Society, pp. 3294, 1955.
Acker, "Syntheses of Reduced Lipoic Acid and Analogs of Lipoic Acid", Journal of Organic Chemistry, vol. 28, pp. 2533-2536, 1963.
Katritzky et al., "Polymers by the Reaction of Bis(pyrylium Salts) with Diamines: A Novel Approach to Ionene Polymers", Journal of Polymer Science: Part A: Polymer Chemistry, vol. 26, pp. 3323-3336, 1988.
Ito et al., "One-pot Synthesis of Cyclophane-type Macrocycles Using Manganese(III)-mediated Oxidative Radical Cyclization", Organic & Biomolecular Chemistry, vol. 9, No. 5, pp. 1491-1507, 2011.
Ito et al., "Supplementary Data: One-pot Synthesis of Cyclophane-type Macrocycles Using Manganese(III)-mediated Oxidative Radical Cyclization", Supplementary Material (ESI) for Organic & Biomolecular Chemistry, pp. 1-11, 2011.
Database CA [Online] Chemical Abstracts Service, Columbus, Ohio, US; XP002679494, Database accession No. 85:192312 abstract.

* cited by examiner

*Primary Examiner* — Brian P Mruk
(74) *Attorney, Agent, or Firm* — Thomas G. Krivulka

(57) ABSTRACT

Fragrances having a fresh character are usually very volatile and therefore not very economical in typical applications such as washing or cleaning processes for example. For that reason they have to be used in relatively large amounts in order to bring about appropriate effects. The present invention describes photolabile pro-fragrances that allow for a greatly improved persistence of the fragrance impression, in particular one having a fresh character, in typical applications. A more economical use of the fragrances in question can be ensured in this way.

6 Claims, No Drawings

PHOTOLABILE PRO-FRAGRANCES

FIELD OF THE INVENTION

The present invention generally relates to special ketones that function as photolabile pro-fragrances. The present invention also relates to washing or cleaning agents containing such ketones. It also relates to a method for the lasting fragrancing of surfaces.

BACKGROUND OF THE INVENTION

Washing or cleaning agents mostly contain fragrances which impart a pleasant odor to the agents. The fragrances mostly mask the odor of the other ingredients, creating a pleasant odor impression for the user.

In the washing agents sector in particular, fragrances (referred to synonymously also as perfumes) are important constituents of the composition, since in both the wet and the dry state the laundry should have a pleasant and where possible also a fresh scent. The fundamental problem underlying the use of fragrances is that they are more or less highly volatile compounds, yet a lasting fragrance effect is desired. In the case in particular of fragrances which provide the fresh and light notes of the perfume and which because of their high vapor pressure evaporate particularly quickly, the desired persistence of the fragrance impression is very difficult to achieve.

A delayed fragrance release can occur through for example the carrier-bound use of fragrances. A carrier-bound precursor form of a fragrance is also known as a pro-fragrance or fragrance storage substance. In this context international patent application WO2007/087977 discloses the use of 1-aza-3,7-dioxabicyclo[3.3.0]octane compounds as pro-fragrances for the delayed release of fragrance aldehydes and fragrance ketones by hydrolysis. An alternative possibility for the delayed release of fragrances is the use of photoactivatable substances as pro-fragrances. Exposure to sunlight or to another electromagnetic radiation source of a certain wavelength induces the breakage of a covalent bond in the pro-fragrance molecule, causing a fragrance to be released.

U.S. Pat. No. 6,949,680 discloses the use of certain phenyl or pyridyl ketones as photoactivatable substances which in the presence of light in a photochemical fragmentation release a terminal alkene as an active substance. Said active substance has for example a fragrance-imparting or antimicrobial activity, which is first delayed by the photochemically induced decomposition and is released over an extended period on a specific surface.

WO2009/118219 A1 describes certain ketones as photoactivatable substances which allow the delayed release of cyclic compounds having at least one cyclic double bond, in particular cyclic terpenes or cyclic terpenoids having at least one cyclic double bond.

WO2010/066486 A2 describes certain beta-hydroxyketones as photoactivatable substances which in the presence of light allow for a release of fragrance aldehydes (perfume aldehydes) and fragrance ketones (perfume ketones).

The object of the present invention was to provide further photoactivatable substances as pro-fragrances which allow for the delayed release of perfume ketones, in particular of damascone.

Furthermore, other desirable features and characteristics of the present invention will become apparent from the subsequent detailed description of the invention and the appended claims, taken in conjunction with the accompanying drawings and this background of the invention.

BRIEF SUMMARY OF THE INVENTION

A compound of the general formula (I),

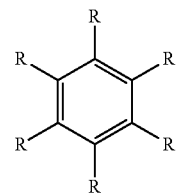

Formula (I)

wherein at least two of the residues R in formula (I) denote the residue a shown in square brackets,

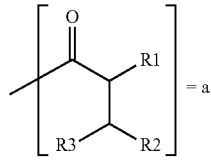

= a and wherein the remaining residues R in formula (I), independently of one another, each denote hydrogen, a halogen atom, —$NO_2$, a linear or branched, substituted or unsubstituted alkoxy group having 1 to 15 C atoms, a linear or branched, substituted or unsubstituted alkyl group having 1 to 15 C atoms, an aryl residue, a cycloalkyl residue, acyl residue, —OH, —NH alkyl, —$NH_2$ or —$N(alkyl)_2$, and wherein for each residue a set in square brackets, independently of one another; R2 denotes a substituted hydrocarbon residue having at least one C=O group; R1 and R3, independently of one another, each denote hydrogen, a halogen atom, —$NO_2$, a linear or branched, substituted or unsubstituted alkoxy group having 1 to 15 C atoms, a linear or branched, substituted or unsubstituted alkyl group having 1 to 15 C atoms, an aryl residue, a cycloalkyl residue, acyl residue, —OH, —NH alkyl, —$NH_2$ or —$N(alkyl)_2$.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

The object of the present invention was achieved by a compound of the general formula (I),

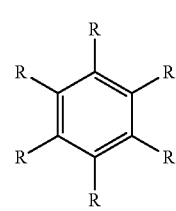

Formula (I)

wherein at least two of the residues R in formula (I) denote the residue a shown in square brackets,

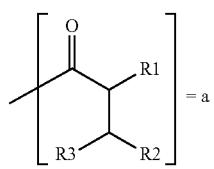

and wherein the remaining residues R in formula (I), independently of one another, each denote hydrogen, a halogen atom, —NO$_2$, a linear or branched, substituted or unsubstituted alkoxy group having 1 to 15 C atoms, a linear or branched, substituted or unsubstituted alkyl group having 1 to 15 C atoms, an aryl residue, a cycloalkyl residue, acyl residue, —OH, —NH alkyl, —NH$_2$ or —N(alkyl)$_2$,
and wherein for each residue a set in square brackets, independently of one another, R2 denotes a substituted hydrocarbon residue having at least one C═O group, R1 and R3, independently of one another, each denote hydrogen, a halogen atom, —NO$_2$, a linear or branched, substituted or unsubstituted alkoxy group having 1 to 15 C atoms, a linear or branched, substituted or unsubstituted alkyl group having 1 to 15 C atoms, an aryl residue, a cycloalkyl residue, acyl residue, —OH, —NH alkyl, —NH$_2$ or —N(alkyl)$_2$.

The residue R2, which denotes a substituted hydrocarbon residue having at least one C═O group, can be linear or branched and in particular it can also encompass at least one ring system.

The compounds according to the invention of the general formula (I) are ketones, so they are also referred to below as ketones according to the invention or as ketones according to the invention of formula (I). Surprisingly it has been found that the ketones according to the invention are particularly effective pro-fragrances, which allow for the delayed release of perfume ketones, in particular of damascone. The use of the ketones according to the invention in washing, cleaning or care agents led to an improved long-term fragrance effect in the use thereof, in particular in connection with the treatment of textiles. When, for example, ketones according to the invention were used in a laundry treatment agent such as for example a washing agent or fabric softener, an improved long-term fragrance effect in the treated laundry was found. Corresponding products also have a particularly good storage stability. The agents according to the invention also enable the total amount of perfume contained in the agent to be reduced while nevertheless achieving olfactory benefits in the laundered textiles, in particular with regard to the perception of freshness. The favorable ratio of releasable perfumes to anchor molecule is also particularly advantageous. At least two molecules of perfume are released per carrier molecule. This allows for a particularly effective use for fragrancing purposes. The excellent long-term fragrance effect appears to be explainable by the fact that when the stored perfumes are released on the target substrate the process proceeds successively, in other words one (or more) bound perfume molecule still acts as an anchor while another perfume molecule has already been released.

It is also possible that individual residues R of the ketone of the general formula (I) are bridged between one another to form cyclic compounds, for example via C, O, N or S atoms.

According to the invention it is particularly preferable that in the residue a R1 denotes hydrogen or a linear or branched, substituted or unsubstituted alkyl group having 1 to 6 C atoms, in particular a methyl group. It is likewise preferable that in the residue a R3 denotes hydrogen or a linear or branched, substituted or unsubstituted alkyl group having 1 to 6 C atoms, in particular a methyl group.

The residues a with which the benzene ring in formula (I) is substituted can in each case be identical or different. In a preferred embodiment said residues a are identical. This embodiment is particularly advantageous if a particularly intensive odor of a certain perfume is to be produced. The embodiment in which different residues a are used is particularly advantageous when mixed odors are desired.

Two of the residues R in formula (I) preferably denote the residue a set in square brackets, but that number can also be higher, for example three or four of the residues R in formula (I) can denote the residue a set in square brackets.

If there are two residues R in formula (I) according to the residue a set in square brackets, they are preferably in the 1,4-position on the benzene ring in respect of one another. If there are three residues R in formula (I) according to the residue a set in square brackets, they are preferably in the 1,3,5-position on the benzene ring in respect of one another.

In a preferred embodiment of the invention all other residues R on the benzene ring in formula (I) that do not correspond to the residue a set in square brackets denote hydrogen.

The ketone according to the invention of the general formula (I) is suitable as a pro-fragrance for all conventional fragrance ketones, selected in particular from Buccoxime; isojasmone; methyl-beta-naphthyl ketone; musk indanone; Tonalide/Musk plus; alpha-damascone, beta-damascone, delta-damascone, gamma-damascone, damascenone, damarose, methyl dihydrojasmonate, menthone, carvone, camphor, fenchone, alpha-ionone, beta-ionone, gamma-methyl ionone, fleuramone, dihydrojasmone, cis-jasmone, iso-E-Super®, methyl cedrenyl ketone or methyl cedrylone, acetophenone, methyl acetophenone, para-methoxyacetophenone, methyl-beta-naphthyl ketone, benzyl acetone, benzophenone, para-hydroxyphenyl butanone, celery ketone or livescone, 6-isopropyl decahydro-2-naphthone, dimethyl octenone, frescomenthe, 4-(1-ethoxyvinyl)-3,3,5,5-tetramethylcyclohexanone, methyl heptenone, 2-(2-(4-methyl-3-cyclohexen-1-yl)propyl)cyclopentanone, 1-(p-menthen-6(2)yl)-1-propanone, 4-(4-hydroxy-3-methoxyphenyl)-2-butanone, 2-acetyl-3,3-dimethyl norbornane, 6,7-dihydro-1,1,2,3,3-pentamethyl-4(5H)indanone, 4-damascol, dulcinyl or cassione, gelsone, hexylon, isocyclemone E, methyl cyclocitrone, methyl lavender ketone, orivone, para-tert-butyl cyclohexanone, Verdon, Delphone, muscone, neobutenone, plicatone, Veloutone, 2,4,4,7-tetramethyl oct-6-en-3-one, tetrameran or mixtures thereof. The ketones can preferably be selected from the damascones, carvone, gamma-methyl ionone, iso-E-Super, 2,4,4,7-tetramethyl oct-6-en-3-one, benzyl acetone, damascenone, methyl dihydrojasmonate, methyl cedrylone, hedione and mixtures thereof. All damascones and damascenones are most preferred.

The stored ketones can be released from the compound according to the invention of formula (I) under exposure to electromagnetic radiation, in particular encompassing wavelengths from 200 to 400 nm.

According to a particularly preferred embodiment the ketone according to the invention of formula (I) is a compound in which two of the residues R correspond to the specified residue a set in square brackets and are in the 1,4-position in respect of one another, wherein they are the same residue a, and wherein the other four residues R denote hydrogen, and wherein the residues a are preferably chosen such that under exposure to light, in particular encompassing wavelengths from 200 to 400 nm, the ketone according to the invention releases one of the fragrance ketones listed by name above, in particular fragrance ketones of the damascone type.

According to a preferred embodiment the residue a set in square brackets corresponds to the following residue b:

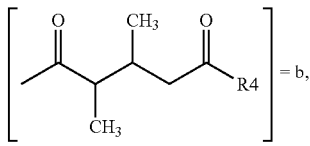

wherein the residue R4 denotes an optionally substituted hydrocarbon residue having at least 5 C atoms, which encompasses in particular a cyclic hydrocarbon residue.

Particularly preferred residues b correspond to the following residues b1 to b5:

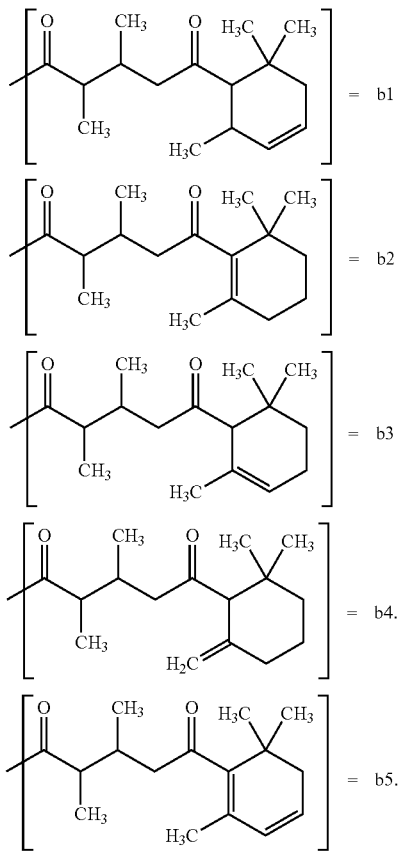

Preferred ketones according to the invention of formula (I) encompass 2 or 3 of the residues b1 to b5, the other residues R denoting hydrogen. Particularly preferred ketones according to the invention of formula (I) encompass 2 identical residues selected from b1 to b5, said residues preferably being in the 1,4-position in respect of one another, the other residues R denoting hydrogen.

Correspondingly, an example of a particularly preferred ketone according to the invention is shown below:

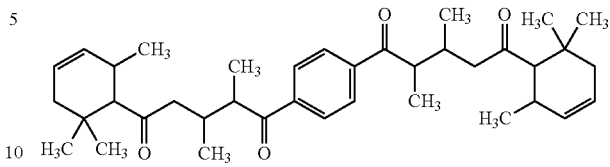

The ketones according to the invention of the aforementioned formulae can be incorporated very stably into the conventional washing or cleaning agent matrices, into cosmetics and into existing perfume compositions. They allow for a delayed release of the stored fragrances, namely in particular of damascone in the α, β, γ or δ form and of damascenone, in particular β-damascenone. Said ketones impart a particularly long-lasting freshness impression to conventional washing or cleaning agents and to cosmetics. The dried, laundered textile in particular benefits from the good long-term fresh fragrance effect. The slow release of the stored perfume takes place following exposure to light (electromagnetic radiation), in particular encompassing wavelengths from 200 to 400 nm, as illustrated in simplified terms in the reaction equation below:

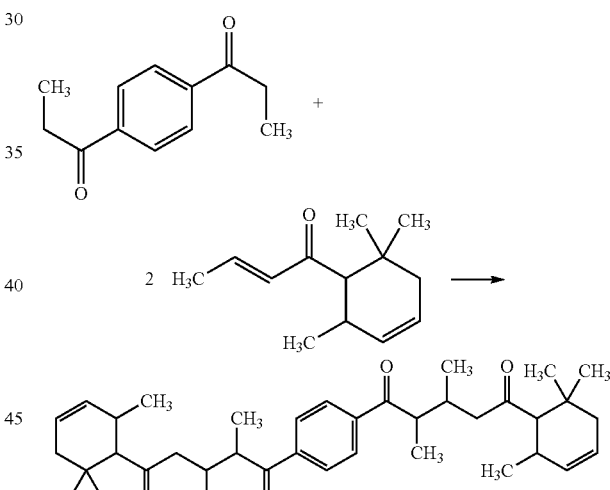

The present invention also provides a washing or cleaning agent, preferably a washing agent, fabric softener or washing auxiliary agent, containing at least one ketone according to the invention of formula (I), wherein said ketone is preferably contained in amounts of between 0.0001 and 5 wt. %, advantageously between 0.001 and 4 wt. %, more advantageously between 0.01 and 3 wt. %, in particular between 0.1 and 2 wt. %, relative in each case to the total agent. Suitable cleaning agents are for example cleaning agents for hard surfaces, such as preferably dishwashing agents. They can likewise be cleaning agents such as for example household cleaners, general purpose cleaners, window cleaners, floor cleaners, etc. They can preferably be a product for cleaning lavatory pans and urinals, advantageously a toilet freshener to hang in the lavatory pan, in particular a toilet rim block.

According to a preferred embodiment of the invention the washing or cleaning agent according to the invention contains at least one surfactant selected from anionic, cationic, non-ionic, zwitterionic, amphoteric surfactants or mixtures thereof.

According to a further preferred embodiment of the invention the agent according to the invention is in solid or liquid form.

The invention also provides a cosmetic agent containing at least one ketone of formula (I), which cosmetic agent preferably contains said ketone in amounts of between 0.0001 and 5 wt. %, advantageously between 0.001 and 4 wt. %, more advantageously between 0.01 and 3 wt. %, in particular between 0.1 and 2 wt. %, relative in each case to the total agent.

The invention also provides an air care agent (e.g. room air freshener, room deodorizer, room spray, etc.) containing at least one ketone of formula (I), wherein said ketone is preferably contained in amounts of between 0.0001 and 50 wt. %, advantageously between 0.001 and 5 wt. %, more advantageously between 0.1 and 3 wt. %, in particular between 0.1 and 2 wt. %, relative in each case to the total agent.

According to a further preferred embodiment of the invention an agent according to the invention (i.e. washing or cleaning agent, cosmetic agent or air care agent), in particular washing or cleaning agent, contains additional fragrances, preferably in amounts from 0.00001 to 5 wt. %, selected in particular from the group encompassing fragrances of natural or synthetic origin, preferably more highly volatile fragrances, higher-boiling fragrances, solid fragrances and/or fixative fragrances.

Fixative perfumes, which can advantageously be used in the context of the present invention, are for example essential oils such as angelica root oil, aniseed oil, arnica flower oil, basil oil, bay oil, bergamot oil, champaca flower oil, noble fir oil, noble fir cone oil, elemi oil, eucalyptus oil, fennel oil, spruce needle oil, galbanum oil, geranium oil, gingergrass oil, guaiac wood oil, gurjun balsam oil, *helichrysum* oil, hon-sho oil, ginger oil, iris oil, cajeput oil, calamus oil, chamomile oil, camphor oil, cananga oil, cardamom oil, *cassia* oil, pine needle oil, copaiba balsam oil, coriander oil, spearmint oil, caraway oil, cumin oil, lavender oil, lemongrass oil, lime oil, mandarin oil, melissa oil, musk seed oil, myrrh oil, clove oil, neroli oil, niaouli oil, olibanum oil, orange oil, *origanum* oil, palmarosa oil, patchouli oil, Peru balsam oil, petitgrain oil, pepper oil, peppermint oil, pimento oil, pine oil, rose oil, rosemary oil, sandalwood oil, celery oil, spike lavender oil, star anise oil, turpentine oil, *thuja* oil, thyme oil, verbena oil, vetiver oil, juniper berry oil, wormwood oil, wintergreen oil, ylang-ylang oil, hyssop oil, cinnamon oil, cinnamon leaf oil, citronella oil, lemon oil and cypress oil.

However, higher-boiling or solid perfumes of natural or synthetic origin can also be used in the context of the present invention as fixative perfumes or perfume blends, i.e. as fragrances. These compounds include the compounds listed below and mixtures thereof: ambrettolide, α-amylcinnamaldehyde, anethol, anisaldehyde, anisic alcohol, anisol, methyl anthranilate, acetophenone, benzyl acetone, benzaldehyde, ethyl benzoate, benzophenone, benzyl alcohol, benzyl acetate, benzyl benzoate, benzyl formate, benzyl valerianate, borneol, bornyl acetate, α-bromostyrene, n-decyl aldehyde, n-dodecyl aldehyde, eugenol, eugenol methyl ether, eucalyptol, farnesol, fenchone, fenchyl acetate, geranyl acetate, geranyl formate, heliotropin, methyl heptine carboxylate, heptaldehyde, hydroquinone dimethyl ether, hydroxycinnamaldehyde, hydroxycinnamic alcohol, indole, irone, isoeugenol, isoeugenol methyl ether, isosafrole, jasmone, camphor, carvacrol, carvone, p-cresol methyl ether, coumarin, p-methoxyacetophenone, methyl-n-amyl ketone, methyl methyl anthranilate, p-methyl acetophenone, methyl chavicol, p-methyl quinoline, methyl-β-naphthyl ketone, methyl-n-nonyl acetaldehyde, methyl-n-nonyl ketone, muscone, β-naphthol ethyl ether, β-naphthol methyl ether, nerol, nitrobenzene, n-nonyl aldehyde, nonyl alcohol, n-octyl aldehyde, p-oxyacetophenone, pentadecanolide, β-phenyl ethyl alcohol, phenyl acetaldehyde dimethyl acetal, phenyl acetic acid, pulegone, safrole, isoamyl salicylate, methyl salicylate, hexyl salicylate, cyclohexyl salicylate, santalol, skatole, terpineol, thymene, thymol, γ-undelactone, vanillin, veratrum aldehyde, cinnamaldehyde, cinnamyl alcohol, cinnamic acid, ethyl cinnamate, benzyl cinnamate. The more highly volatile fragrances include in particular the lower-boiling perfumes of natural or synthetic origin, which can be used alone or in mixtures. Examples of more highly volatile fragrances are alkyl isothiocyanates (alkyl mustard oils), butanedione, limonene, linalool, linalyl acetate and propionate, menthol, menthone, methyl-n-heptenone, phellandrene, phenylacetaldehyde, terpinyl acetate, citral, citronellal.

According to a further preferred embodiment the agent according to the invention (i.e. washing or cleaning agent, cosmetic agent or air care agent), in particular washing or cleaning agent, has at least one, preferably a plurality of, active components, in particular active washing components, active care components, active cleaning components and/or cosmetic components, advantageously selected from the group encompassing anionic surfactants, cationic surfactants, amphoteric surfactants, non-ionic surfactants, acidifying agents, alkalizing agents, anti-crease compounds, antibacterial substances, antioxidants, anti-redeposition agents, antistatics, builder substances, bleaching agents, bleach activators, bleach stabilizers, bleach catalysts, ironing aids, cobuilders, fragrances, anti-shrink agents, electrolytes, enzymes, color protecting agents, coloring agents, dyes, dye transfer inhibitors, fluorescent agents, fungicides, germicides, odor-complexing substances, auxiliary agents, hydrotropes, rinse aids, complexing agents, preservatives, corrosion inhibitors, water-miscible organic solvents, optical brighteners, perfumes, perfume carriers, pearling agents, pH adjusters, phobing and impregnating agents, polymers, non-swelling agents, anti-slip agents, foam inhibitors, layered silicates, dirt-repellent substances, silver protection agents, silicone oils, soil release active agents, UV protective substances, viscosity regulators, thickening agents, discoloration inhibitors, graying inhibitors, vitamins and/or fabric softeners. Within the meaning of this invention, stated amounts for the agent according to the invention in wt. %, unless otherwise specified, relate to the total weight of the agent according to the invention.

The amounts of individual ingredients in the agents according to the invention (i.e. washing or cleaning agent, cosmetic agent or air care agent), in particular washing or cleaning agent, are guided in each case by the intended use of the agents in question, and the person skilled in the art is familiar in principle with the orders of magnitude of the amounts of ingredients to use or can obtain them from the associated specialist literature. Depending on the intended use of the agents according to the invention, a higher or lower surfactant content, for example, will be chosen. For example, the surfactant content of washing agents, for example, can conventionally be between 10 and 50 wt. %, preferably between 12.5 and 30 wt. % and in particular between 15 and 25 wt. %, whereas cleaning agents for automatic dishwashing, for example, can contain between 0.1 and 10 wt. %, preferably between 0.5 and 7.5 wt. % and in particular between 1 and 5 wt. % of surfactants.

The agents according to the invention (i.e. washing or cleaning agent, cosmetic agent or air care agent), in particular washing or cleaning agent, can contain surfactants, with anionic surfactants, non-ionic surfactants and mixtures thereof, but also cationic surfactants, being preferably suitable. Suitable non-ionic surfactants are in particular ethoxylation and/or propoxylation products of alkyl glycosides and/or linear or branched alcohols each having 12 to 18 C atoms in the alkyl part and 3 to 20, preferably 4 to 10, alkyl ether groups. Corresponding ethoxylation and/or propoxylation products of N-alkylamines, vicinal diols, fatty acid esters and fatty acid amides, which in terms of the alkyl part correspond to the cited long-chain alcohol derivatives, and of alkyl phenols having 5 to 12 C atoms in the alkyl residue can also be used.

Suitable anionic surfactants are in particular soaps and examples containing sulfate or sulfonate groups, with preferably alkali ions as cations. Soaps which can be used are preferably the alkali salts of saturated or unsaturated fatty acids having 12 to 18 C atoms. Such fatty acids can also be used in not completely neutralized form. Suitable surfactants of the sulfate type include the salts of sulfuric acid semi-esters of fatty alcohols having 12 to 18 C atoms and the sulfation products of said non-ionic surfactants with a low degree of ethoxylation. Suitable surfactants of the sulfonate type include linear alkylbenzene sulfonates having 9 to 14 C atoms in the alkyl part, alkane sulfonates having 12 to 18 C atoms, and olefin sulfonates having 12 to 18 C atoms which are formed in the reaction of corresponding monoolefins with sulfur trioxide, as well as alpha-sulfo fatty acid esters which are formed in the sulfonation of fatty acid methyl or ethyl esters.

Cationic surfactants are preferably selected from the esterquats and/or the quaternary ammonium compounds according to the general formula $(R^I)(R^{II})(R^{III})(R^{IV})N^+X^-$, in which $R^I$ to $R^{IV}$ denote identical or different $C_{1-22}$ alkyl residues, $C_{7-28}$ arylalkyl residues or heterocyclic residues, wherein two or in the case of an aromatic bonding as in pyridine even three residues together with the nitrogen atom form the heterocycle, for example a pyridinium or imidazolinium compound, and $X^-$ denotes halide ions, sulfate ions, hydroxide ions or similar anions. Quaternary ammonium compounds can be produced by reacting tertiary amines with alkylating agents, such as for example methyl chloride, benzyl chloride, dimethyl sulfate, dodecyl bromide, but also ethylene oxide. The alkylation of tertiary amines having one long alkyl residue and two methyl groups is achieved particularly easily; in addition, the quaternization of tertiary amines having two long residues and one methyl group can be performed under gentle conditions with the aid of methyl chloride. Amines having three long alkyl residues or hydroxy-substituted alkyl residues are not very reactive and are quaternized with dimethyl sulfate, for example. Suitable quaternary ammonium compounds are for example benzalkonium chloride (N-alkyl-N,N-dimethyl benzylammonium chloride), benzalkon B (m,p-dichlorobenzyldimethyl-$C_{12}$-alkylammonium chloride, benzoxonium chloride (benzyldodecyl bis-(2-hydroxyethyl)ammonium chloride), cetrimonium bromide (N-hexadecyl-N,N-trimethylammonium bromide), benzetonium chloride (N,N-dimethyl-N-[2-[2-[p-(1,1,3,3-tetramethylbutyl)phenoxy]ethoxy]ethyl]benzylammonium chloride), dialkyldimethylammonium chlorides such as di-n-decyldimethylammonium chloride, didecyldimethylammonium bromide, dioctyldimethylammonium chloride, 1-cetylpyridinium chloride and thiazoline iodide and mixtures thereof. Preferred quaternary ammonium compounds are benzalkonium chlorides having $C_8$-$C_{22}$ alkyl residues, in particular $C_{12}$-$C_{14}$ alkylbenzyldimethylammonium chloride.

Preferred esterquats are methyl-N-(2-hydroxyethyl)-N,N-di(tallow acyloxyethyl)ammonium methosulfate, bis-(palmitoyl)ethyl hydroxyethyl methylammonium methosulfate or methyl-N,N-bis(acyloxyethyl)-N-(2-hydroxyethyl)ammonium methosulfate.

Surfactants are contained in the agents according to the invention (i.e. washing or cleaning agent, cosmetic agent or air care agent), in particular washing or cleaning agent, in quantitative proportions of preferably 5 wt. % to 50 wt. %, in particular 8 wt. % to 30 wt. %. In laundry post-treatment agents in particular, up to 30 wt. % of surfactants are preferably used, in particular 5 wt. % to 15 wt. %, preferably including at least a proportion of cationic surfactants.

An agent according to the invention, in particular washing or cleaning agent, preferably contains at least one water-soluble and/or water-insoluble, organic and/or inorganic builder. The water-soluble organic builder substances include polycarboxylic acids, in particular citric acid and sugar acids, monomeric and polymeric aminopolycarboxylic acids, in particular methylglycine diacetic acid, nitrilotriacetic acid and ethylenediamine tetraacetic acid as well as polyaspartic acid, polyphosphonic acids, in particular amino tris(methylene phosphonic acid), ethylenediamine tetrakis(methylene phosphonic acid) and 1 hydroxyethane-1,1-diphosphonic acid, polymeric hydroxy compounds such as dextrin as well as polymeric (poly)carboxylic acids, polymeric acrylic acids, methacrylic acids, maleic acids and mixed polymers thereof, which can also contain small amounts of polymerizable substances without carboxylic acid functionality incorporated by polymerization. For the production of liquid agents in particular, the organic builder substances can be used in the form of aqueous solutions, preferably in the form of 30 to 50 wt. % aqueous solutions. All the cited acids are generally used in the form of their water-soluble salts, in particular their alkali salts.

Organic builder substances can be included if desired in amounts of up to 40 wt. %, in particular up to 25 wt. % and preferably from 1 wt. % to 8 wt. %. Amounts close to the cited upper limit are preferably used in paste-form or liquid, in particular water-containing, agents according to the invention. Laundry post-treatment agents according to the invention, such as fabric softeners for example, can optionally also be free from organic builders.

Suitable water-soluble inorganic builder materials include in particular alkali silicates and polyphosphates, preferably sodium triphosphate. Crystalline or amorphous alkali aluminosilicates in particular can be used as water-insoluble, water-dispersible inorganic builder materials, if desired in amounts of up to 50 wt. %, preferably not over 40 wt. % and in liquid agents in particular in amounts of 1 wt. % to 5 wt. %. Of these the crystalline sodium aluminosilicates in washing agent grade, in particular Zeolite A, P and optionally X, are preferred. Amounts close to the cited upper limit are preferably used in solid, particulate agents. Suitable aluminosilicates have in particular no particles with a particle size of more than 30 μm and preferably consist of at least 80 wt. % of particles with a size of less than 10 μm. It is, however, particularly preferable to avoid the use of water-insoluble builder materials, to a very great extent at least, such that they are preferably used, if at all, in only small amounts, for example in amounts of <5 wt. % or <1 wt. %, relative to the total agent.

Suitable substitutes or partial substitutes for said aluminosilicate are crystalline alkali silicates, which can be present alone or mixed with amorphous silicates. The alkali silicates that can be used as builders in the agents according to the invention preferably have a molar ratio of alkali oxide to $SiO_2$ of less than 0.95, in particular from 1:1.1 to 1:12, and can be amorphous or crystalline. Preferred alkali silicates are the sodium silicates, in particular the amorphous sodium silicates, with a molar ratio of $Na_2O:SiO_2$ of 1:2 to 1:2.8. Crystalline layered silicates of the general formula $Na_2Si_xO_{2x+1} \cdot y\ H_2O$ are preferably used as crystalline silicates, which can be present alone or mixed with amorphous silicates, in which x, the modulus, is a number from 1.9 to 4 and y is a number from 0 to 20, and preferred values for x are 2, 3 or 4. Preferred crystalline layered silicates are those in which x assumes the values 2 or 3 in the cited general formula. In particular both β- and δ-sodium disilicates ($Na_2Si_2O_5 \cdot y\ H_2O$) are preferred. Virtually anhydrous crystalline alkali silicates of the aforementioned general formula prepared from amorphous alkali silicates, in which x denotes a number from 1.9 to 2.1, can also be used in agents according to the invention. In a further preferred embodiment of agents according to the invention a crystalline sodium layered silicate with a modulus of 2 to 3 is used, such as can be prepared from sand and soda. Crystalline sodium silicates with a modulus in the range from 1.9 to 3.5 are used in a further preferred embodiment of agents according to the invention. If alkali aluminosilicate, in particular zeolite, is also present as an additional builder substance, the weight ratio of aluminosilicate to silicate, relative in each case to anhydrous active substances, is preferably 1:10 to 10:1. In agents containing both amorphous and crystalline alkali silicates, the weight ratio of amorphous alkali silicate to crystalline alkali silicate is preferably 1:2 to 2:1 and in particular 1:1 to 2:1.

If desired, builder substances are preferably contained in the agents according to the invention, in particular washing or cleaning agents, in amounts of up to 60 wt. %, in particular 5 wt. % to 40 wt. %. Laundry post-treatment agents according to the invention, such as fabric softeners for example, are preferably free from inorganic builders.

Suitable peroxygen compounds are in particular organic peracids or peracid salts of organic acids, such as phthalimidoperhexanoic acid, perbenzoic acid or salts of diperdodecanedioic acid, hydrogen peroxide and inorganic salts which give off hydrogen peroxide under the application conditions, such as perborate, percarbonate and/or persilicate. If solid peroxygen compounds are to be used, they can be used in the form of powders or granules, which can also be coated in a manner known in principle. Alkali percarbonate, alkali perborate monohydrate or, in liquid agents in particular, hydrogen peroxide in the form of aqueous solutions containing 3 wt. % to 10 wt. % of hydrogen peroxide are particularly preferably optionally used. If an agent according to the invention contains bleaching agents, such as preferably peroxygen compounds, these are present in amounts of preferably up to 50 wt. %, in particular from 5 wt. % to 30 wt. %. The addition of small amounts of known bleaching agent stabilizers such as for example phosphonates, borates or metaborates and metasilicates as well as magnesium salts such as magnesium sulfate can be useful.

Compounds which under perhydrolysis conditions yield aliphatic peroxocarboxylic acids having preferably 1 to 10 C atoms, in particular 2 to 4 C atoms, and/or optionally substituted perbenzoic acid can be used as bleach activators. Substances bearing O and/or N acyl groups of the cited C atomic number and/or optionally substituted benzoyl groups are suitable. Polyacylated alkylene diamines, in particular tetraacetyl ethylenediamine (TAED), acylated triazine derivatives, in particular 1,5-diacetyl-2,4-dioxohexahydro-1,3,5-triazine (DADHT), acylated glycolurils, in particular tetraacetyl glycoluril (TAGU), N-acylimides, in particular N-nonanoyl succinimide (NOSI), acylated phenol sulfonates, in particular n-nonanoyl or isononanoyl oxybenzene sulfonate (n- or iso-NOBS), carboxylic anhydrides, in particular phthalic anhydride, acylated polyhydric alcohols, in particular triacetin, ethylene glycol diacetate, 2,5-diacetoxy-2,5-dihydrofuran and enol esters, as well as acetylated sorbitol and mannitol or mixtures thereof (SORMAN), acylated sugar derivatives, in particular pentaacetyl glucose (PAG), pentaacetyl fructose, tetraacetyl xylose and octaacetyl lactose, as well as acetylated, optionally N-alkylated glucamine and gluconolactone, and/or N-acylated lactams, for example N-benzoyl caprolactam, are preferred.

Hydrophilically substituted acyl acetals and acyl lactams are likewise preferably used. Combinations of conventional bleach activators can also be used. Such bleach activators can be included in the conventional range of amounts, preferably in amounts from 1 wt. % to 10 wt. %, in particular 2 wt. % to 8 wt. %, relative to the total agent.

Sulfonimines and/or bleach-reinforcing transition metal salts or transition metal complexes can also be included as so-called bleach catalysts in addition to the aforementioned conventional bleach activators or in their place.

Suitable enzymes for use in the agents include those from the class of proteases, cutinases, amylases, pullulanases, hemicellulases, cellulases, lipases, oxidases and peroxidases as well as mixtures thereof. Enzymatic active ingredients obtained from fungi or bacteria, such as *Bacillus subtilis, Bacillus licheniformis, Streptomyces griseus, Humicola lanuginosa, Humicola insolens, Pseudomonas pseudoalcaligenes* or *Pseudomonas cepacia*, are particularly suitable. The optionally used enzymes can be adsorbed on supporting materials and/or embedded in coating substances to protect them against premature inactivation. If desired, they are preferably contained in the agents according to the invention in amounts not exceeding 5 wt. %, in particular 0.2 wt. % to 2 wt. %.

As optical brighteners the agents can optionally contain for example derivatives of diaminostilbene disulfonic acid or alkali metal salts thereof. Salts of 4,4'-bis(2-anilino-4-morpholino-1,3,5-triazinyl-6-amino)stilbene-2,2'-disulfonic acid or similarly structured compounds bearing a diethanolamino group, a methylamino group, an anilino group or a 2-methoxyethylamino group in place of the morpholino group, are suitable for example.

Suitable foam inhibitors include for example organopolysiloxanes and mixtures thereof with microfine, optionally silanized silicic acid and paraffin waxes and mixtures thereof with silanized silicic acid or bis-fatty acid alkylene diamides. Mixtures of various foam inhibitors are also used to advantage, for example those comprising silicones, paraffins or waxes. The foam inhibitors, in particular silicone- and/or paraffin-containing foam inhibitors, are preferably bound to a granular, water-soluble or water-dispersible carrier substance. Mixtures of paraffin waxes and bistearyl ethylenediamides are preferred in particular.

In addition, the agents can also contain components known as soil release agents, which positively influence the ability to wash oils and fats out of textiles. This effect becomes particularly apparent if a textile that has previously been washed multiple times with an agent according to the invention containing said oil and fat releasing component is soiled. The preferred oil and fat releasing components include for example non-ionic cellulose ethers such as methyl cellulose and methyl hydroxypropyl cellulose containing from 15 to 30 wt. % of methoxyl groups and from 1 to 15 wt. % of hydroxypropoxyl groups, relative in each case to the non-ionic cellulose ether, and the polymers of phthalic acid and/or terephthalic acid or derivatives thereof with monomeric and/or polymeric diols, in particular polymers of ethylene terephthalates and/or polyethylene glycol terephthalates or anionically and/or non-ionically modified derivatives thereof, known from the prior art.

The agents can also contain dye transfer inhibitors, preferably in amounts from 0.1 wt. % to 2 wt. %, in particular 0.1 wt. % to 1 wt. %, which in a preferred embodiment of the invention are polymers of vinyl pyrrolidone, vinyl imidazole, vinyl pyridine-N-oxide or copolymers thereof.

Graying inhibitors have the task of holding the dirt released from the textile fibers suspended in the liquor. Water-soluble colloids, mostly of an organic nature, are suitable for this purpose, for example starch, glue, gelatin, salts of ether carboxylic acids or ether sulfonic acids of starch or cellulose or salts of acid sulfuric acid esters of cellulose or starch. Water-soluble polyamides containing acid groups are also suitable for this purpose. Starch derivatives other than those mentioned above can also be used, for example aldehyde starches. Cellulose ethers such as carboxymethyl cellulose (Na salt), methyl cellulose, hydroxyalkyl cellulose and mixed ethers, such as methylhydroxyethyl cellulose, methylhydroxypropyl cellulose, methylcarboxymethyl cellulose and mixtures thereof can preferably be used, for example in amounts of 0.1 to 5 wt. %, relative to the agents.

The organic solvents that can be used in the agents according to the invention, particularly if they are in liquid or paste form, include alcohols having 1 to 4 C atoms, in particular methanol, ethanol, isopropanol and tert-butanol, diols having 2 to 4 C atoms, in particular ethylene glycol and propylene glycol, and mixtures thereof and the ethers derivable from said classes of compounds. Such water-miscible solvents are preferably present in the agents according to the invention in amounts not exceeding 30 wt. %, in particular 6 wt. % to 20 wt. %.

To set a desired pH that is not established automatically by mixing the other components, the agents according to the invention can contain system-compatible and environmentally compatible acids, in particular citric acid, acetic acid, tartaric acid, malic acid, lactic acid, glycolic acid, succinic acid, glutaric acid and/or adipic acid, but also mineral acids, in particular sulfuric acid, or bases, in particular ammonium or alkali hydroxides. Such pH adjusters are optionally included in the agents according to the invention in amounts preferably not exceeding 20 wt. %, in particular 1.2 wt. % to 17 wt. %.

The production of solid agents according to the invention (i.e. in particular washing or cleaning agents) presents no difficulties and can be performed in principle in a known manner, for example by spray drying or granulation, with optional peroxygen compound and optional bleach catalyst optionally being added at a later stage. A method involving an extrusion step is preferred for the production of agents according to the invention having an elevated bulk density, in particular in the range from 650 g/l to 950 g/l. The production of liquid agents according to the invention likewise presents no difficulties and can likewise be performed in a known manner.

The production of the ketones according to the invention is described in the example section by way of example by reference to the production of a pro-fragrance containing δ-damascone. The other ketones of the general formula (I) are also obtainable via this standard synthesis route.

According to a preferred embodiment the teaching according to the invention can be used to significantly reduce the perfume content in washing, cleaning and personal care agents. In this way it is possible also to offer perfumed products for particularly sensitive consumers who because of specific intolerances and irritations can use normally perfumed products only to a limited extent if at all.

In addition to the ketone according to the invention, a preferred solid, in particular powdered, washing agent according to the invention can also contain in particular components selected for example from the following:

Anionic surfactants, such as preferably alkyl benzene sulfonate, alkyl sulfate, for example in amounts of preferably 5 to 30 wt. %, Non-ionic surfactants, such as preferably fatty alcohol polyglycol ethers, alkyl polyglucoside, fatty acid glucamide, for example in amounts of preferably 0.5 to 15 wt. %, Builders, such as for example zeolite, polycarboxylate, sodium citrate, in amounts of for example 0 to 70 wt. %, advantageously 5 to 60 wt. %, preferably 10 to 55 wt. %, in particular 15 to 40 wt. %, Alkalis, such as for example sodium carbonate, in amounts of for example 0 to 35 wt. %, advantageously 1 to 30 wt. %, preferably 2 to 25 wt. %, in particular 5 to 20 wt. %, Bleaching agents, such as for example sodium perborate, sodium percarbonate, in amounts of for example 0 to 30 wt. %, advantageously 5 to 25 wt. %, preferably 10 to 20 wt. %, Corrosion inhibitors, for example sodium silicate, in amounts of for example 0 to 10 wt. %, advantageously 1 to 6 wt. %, preferably 2 to 5 wt. %, in particular 3 to 4 wt. %, Stabilizers, for example phosphonates, advantageously 0 to 1 wt. %, Foam inhibitor, for example soap, silicone oils, paraffins, advantageously 0 to 4 wt. %, preferably 0.1 to 3 wt. %, in particular 0.2 to 1 wt. %, Enzymes, for example proteases, amylases, cellulases, lipases, advantageously 0 to 2 wt. %, preferably 0.2 to 1 wt. %, in particular 0.3 to 0.8 wt. %, Graying inhibitor, for example carboxymethyl cellulose, advantageously 0 to 1 wt. %, Discoloration inhibitor, for example polyvinyl pyrrolidone derivatives, preferably 0 to 2 wt. %, Adjusters, for example sodium sulfate, advantageously 0 to 20 wt. %, Optical brighteners, for example stilbene derivative, biphenyl derivative, advantageously 0 to 0.4 wt. %, in particular 0.1 to 0.3 wt. %, Optionally further fragrances, Optionally water, Optionally soap, Optionally bleach activators, Optionally cellulose derivatives, Optionally dirt repellents, percentages by weight relative in each case to the total agent.

In another preferred embodiment of the invention the agent is in liquid form, preferably in gel form. Preferred liquid washing or cleaning agents and cosmetics have water contents of for example 10 to 95 wt. %, preferably 20 to 80 wt. % and in particular 30 to 70 wt. %, relative to the total agent. In the case of liquid concentrates the water content can also be particularly low, for example <30 wt. %, preferably <20 wt. %, in particular <15 wt. %, percentages by weight relative in each case to the total agent. The liquid agents can also contain non-aqueous solvents.

In addition to the ketone according to the invention, a preferred liquid, in particular gel-form, washing agent according to the invention can also contain in particular components selected for example from the following:
- Anionic surfactants, such as preferably alkyl benzene sulfonate, alkyl sulfate, for example in amounts of preferably 5 to 40 wt. %,
- Non-ionic surfactants, such as preferably fatty alcohol polyglycol ethers, alkyl polyglucoside, fatty acid glucamide, for example in amounts of preferably 0.5 to 25 wt. %,
- Builders, such as for example zeolite, polycarboxylate, sodium citrate, advantageously 0 to 15 wt. %, preferably 0.01 to 10 wt. %, in particular 0.1 to 5 wt. %,
- Foam inhibitor, for example soap, silicone oils, paraffins, in amounts of for example 0 to 10 wt. %, advantageously 0.1 to 4 wt. %, preferably 0.2 to 2 wt. %, in particular 1 to 3 wt. %,
- Enzymes, for example proteases, amylases, cellulases, lipases, in amounts of for example 0 to 3 wt. %, advantageously 0.1 to 2 wt. %, preferably 0.2 to 1 wt. %, in particular 0.3 to 0.8 wt. %,
- Optical brighteners, for example stilbene derivative, biphenyl derivative, in amounts of for example 0 to 1 wt. %, advantageously 0.1 to 0.3 wt. %, in particular 0.1 to 0.4 wt. %,
- Optionally further fragrances,
- Optionally stabilizers,
- Water
- Optionally soap, in amounts of for example 0 to 25 wt. %, advantageously 1 to 20 wt. %, preferably 2 to 15 wt. %, in particular 5 to 10 wt. %,
- Optionally solvents (preferably alcohols), advantageously 0 to 25 wt. %, preferably 1 to 20 wt. %, in particular 2 to 15 wt. %, percentages by weight relative in each case to the total agent.

In addition to the ketone according to the invention, a preferred liquid fabric softener according to the invention can also contain in particular components selected from the following:
- Cationic surfactants, such as in particular esterquats, for example in amounts of 5 to 30 wt. %,
- Co-surfactants, such as for example glycerol monostearate, stearic acid, fatty alcohols, fatty alcohol ethoxylates, for example in amounts of 0 to 5 wt. %, preferably 0.1 to 4 wt. %,
- Emulsifiers, such as for example fatty amine ethoxylates, for example in amounts of 0 to 4 wt. %, preferably 0.1 to 3 wt. %,
- Optionally further fragrances,
- Dyes, preferably in the ppm range,
- Stabilizers, preferably in the ppm range,
- Solvents such as for example water, in amounts of preferably 60 to 90 wt. %,
percentages by weight relative in each case to the total agent.

The invention also provides a method for the lasting fragrancing of surfaces, wherein a ketone according to formula (I) or a washing or cleaning agent according to the invention is applied to the surface to be fragranced (e.g. textile, crockery, floor) and said surface is then exposed to electromagnetic radiation, in particular encompassing wavelengths from 200 to 400 nm.

The invention also provides a method for lasting room fragrancing, wherein an air care agent according to the invention is exposed to electromagnetic radiation, in particular encompassing wavelengths from 200 to 400 nm.

EXAMPLE

Representation of a ketone of general formula (I):

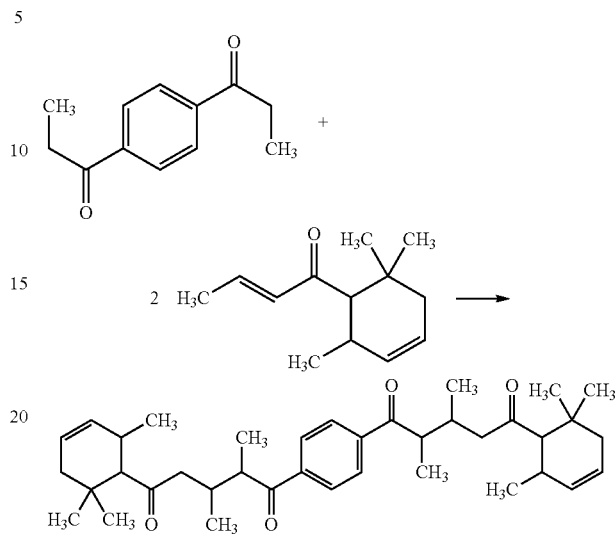

The dilithium enolate of 0.43 g (2.3 mmol) of 1,1'-benzyl-1,4-diyl dipropan-1-one was produced by reaction in 10 ml of anhydrous tetrahydrofuran with 5.1 mmol LDA (comprising 5.1 mmol of diisopropylamine and 6 mmol of a 1.6 M n-BuLi solution in n-hexane, stirred for 1 hour at −78° C. in 15 ml THF) by dropwise addition at −78° C. over a period of 1 hour. At the same temperature the bis-enolate was then mixed with 5.52 mmol of cerium(III) chloride (2.05 g, dried under vacuum) in 15 ml of THF and stirred for 30 min at −78° C. Then 0.96 g of damascone were added dropwise within 30 min while stirring, and the batch was heated to room temperature within 5 hours. The reaction solution was mixed with 40 ml of saturated aqueous ammonium chloride solution and extracted twice with 50 ml of ether. The organic phase was washed with water and saturated NaCl solution and dried over $MgSO_4$. The raw material remaining after drawing off the solvent was purified by washing with pentane. A colorless oil was obtained, which was further purified by column chromatography (mobile solvent petroleum ether:ethyl acetate=95:5). The mono-substituted and di-substituted products were obtained as a mixture in the ratio 1:5 in the form of a colorless oil.

The di-substituted product produced in this way had a very good fragrancing effect when used in washing agents and fabric softeners in textile treatment. In particular, the fragrance impression on the laundry washed therewith and then dried was found to have a better persistence as compared with washing agents and fabric softeners containing an equivalent amount of δ-damascone but of an otherwise identical composition. The fresh fragrance impression of the textiles lasted significantly longer, both after line drying and in particular after drying in an automatic dryer.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A ketone of the general formula (I),

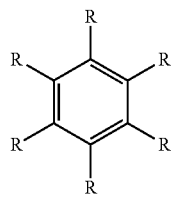

Formula (I)

wherein at least two of the residues R in formula (I), in each case independently, denote the residue b shown in square brackets,

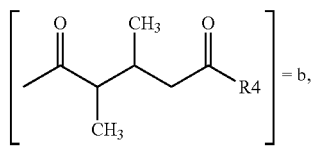

wherein the residue R4 denotes an optionally substituted hydrocarbon residue having at least 5 C atoms;
and wherein the remaining residues R in formula (I), independently of one another, each denote hydrogen, a halogen atom, —NO2, a linear or branched, substituted or unsubstituted alkoxy group having 1 to 15 C atoms, a linear or branched, substituted or unsubstituted alkyl group having 1 to 15 C atoms, an aryl residue, a cycloalkyl residue, acyl residue, —OH, —NH alkyl, —NH$_2$ or —N(alkyl)$_2$.

2. The ketone according to claim 1, wherein the residue b, in each case independently, corresponds to one of the following residues b1 to b5

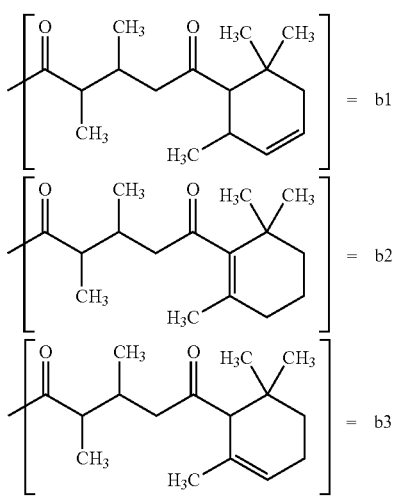

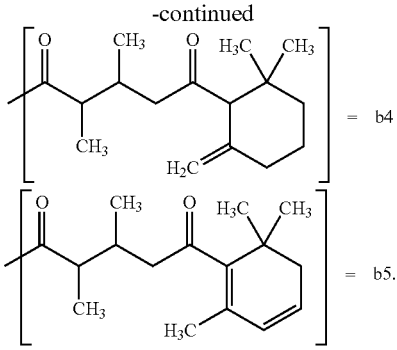

3. A washing or cleaning agent comprising at least one ketone according to the general formula (I),

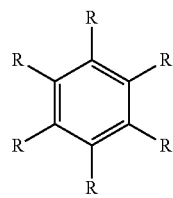

Formula (I)

wherein at least two of the residues R in formula (I) denote the residue a shown in square brackets,

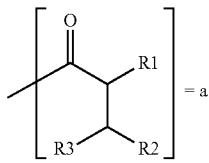

and wherein the remaining residues R in formula (I), independently of one another, each denote hydrogen, a halogen atom, —NO$_2$, a linear or branched, substituted or unsubstituted alkoxy group having 1 to 15 C atoms, a linear or branched, substituted or unsubstituted alkyl group having 1 to 15 C atoms, an aryl residue, a cycloalkyl residue, acyl residue, —OH, —NH alkyl, —NH$_2$ or —N(alkyl)$_2$,
and wherein for each residue a set in square brackets, independently of one another, R2 denotes a substituted hdrocarbon residue having at least one C=O group, R1 and R3, independently of one another, each denote hydrogen, a halogen atom, —NO$_2$, a linear or branched, substituted or unsubstituted alkoxy group having 1 to 15 C atoms, a linear or branched, substituted or unsubstituted alkyl group having 1 to 15 C atoms, an aryl residue, a cycloalkyl residue, acyl residue, —OH, —NH alkyl, —NH$_2$ or —N(alkyl)$_2$;
wherein said ketone is contained in amounts of between 0.0001 and 5 wt. % relative to the total agent.

4. The washing or cleaning agent according to claim 3, wherein it contains at least one surfactant selected from the group consisting of anionic, cationic, non-ionic, zwitterionic, amphoteric surfactants or mixtures thereof.

5. The washing or cleaning agent according to claim 3, wherein it is in solid or liquid form.

6. A method for the lasting fragrancing of surfaces, wherein a ketone according to the general formula (I),

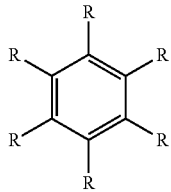

Formula (I)

wherein at least two of the residues R in formula (I) denote the residue a shown in square brackets,

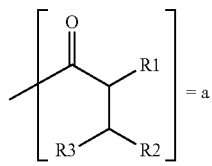

and wherein the remaining residues R in formula (I), independently of one another, each denote hydrogen, a halogen atom, —NO$_2$, a linear or branched, substituted or unsubstituted alkoxy$_{group\ having}$ 1 to 15 C atoms, a linear or branched, substituted or unsubstituted alkyl group having 1 to 15 C atoms, an aryl residue, a cycloalkyl residue, acyl residue, —OH, —NH alkyl, —NH$_2$ or —N(alkyl)$_2$, and wherein for each residue a set in square brackets, independently of one another, R2 denotes a substituted hydrocarbon residue having at least one C=O group, R1 and R3, independently of one another, each denote hydrogen, a halogen atom, —NO$_2$, a linear or branched, substituted or unsubstituted alkoxy group having 1 to 15 C atoms a linear or branched substituted or unsubstituted alk rou havin 1 to 15 C atoms, an aryl residue, a cycloalkyl residue, acyl residue, —OH, —NH alkyl, —NH$_2$ or —N(alkyl)$_2$ is applied to a surface and said surface is then exposed to electromagnetic radiation.

* * * * *